United States Patent [19]
Eason

[11] Patent Number: 5,622,314
[45] Date of Patent: Apr. 22, 1997

[54] GAME SCENT DIFFUSION DEVICE

[76] Inventor: Donald J. Eason, 687 Patosa Trail, Pocahontas, Ark. 72455

[21] Appl. No.: 411,109

[22] Filed: Mar. 27, 1995

[51] Int. Cl.[6] .................................................. A24F 25/00
[52] U.S. Cl. ............................ 239/47; 239/44; 43/1
[58] Field of Search .............................. 239/44, 47, 49, 239/50; 43/1

[56] References Cited

U.S. PATENT DOCUMENTS

| | | | |
|---|---|---|---|
| 2,826,452 | 3/1958 | LeFevre | 239/50 X |
| 4,136,825 | 1/1979 | Mack et al. | 239/50 X |
| 4,742,960 | 5/1988 | Bustillo et al. | 239/47 |

FOREIGN PATENT DOCUMENTS

| | | | |
|---|---|---|---|
| 1176068 | 4/1959 | France | 239/44 |
| 744369 | 2/1956 | United Kingdom | 239/44 |

*Primary Examiner*—Lee W. Young
*Attorney, Agent, or Firm*—Jerry L. Mahurin

[57] ABSTRACT

A Game Scent Diffusion Device adapted to be disposed in a bottle of liquid game scent. The device comprises an inverted "T" shaped member. The member comprises a body portion, defining orifices along its length, and a generally perpendicular crossbar portion. An absorptive wick is woven through the orifices. The ends of the crossbar are springingly, temporarily bent together to facilitate insertion of the device into the bottle. Once the device is inserted into the bottle the crossbar assumes its original shape. When the device is partially withdrawn from the bottle, the ends of the crossbar contact the neck of the bottle. The device can be hung from a convenient location such as a limb. A length of saturated wick and a portion of the saturated wick woven through the orifices in the member are exposed to the ambient air. When not in use the device can be stowed in the bottle, allowing the hunter to carry it in his pocket. The preferred embodiment employs an eyelet disposed within the bottle's cap to anchor the bitter end of the wick. The hunter can handle the cap avoiding contact with the scent on the wick. An alternative embodiment comprises an elongated tab with a central orifice to receive and anchor a wick. The tab is of sufficient length to engage the neck of a scent bottle to prevent removal but narrow enough to allow insertion.

8 Claims, 6 Drawing Sheets

GAME SCENT DIFFUSION DEVICE

BACKGROUND OF THE INVENTION

The present invention broadly relates to hunting. Specifically, the present invention is a Game Scent Diffusion Device. Art pertinent to the subject matter of the present invention can be found in U.S. Patent Class 43, Subclass 1.

The use of scents or lures to attract animals is well known. The use of deer scents such as doe urine to attract deer, particularly bucks, has become more popular in recent years. While baiting game animals is generally illegal, the use of scents is allowed. Such scents are dispensed in a number of ways. Oftentimes, a hunter will use it on his clothing to mask his natural odors. Other times it is distributed at a site to attract game to that location.

Numerous patents have been issued on game or deer scent dispensing or diffusion systems. These prior art devices are primarily of three types. The first drips deer scent on the ground. Gray, U.S. Pat. No. 4,773,177 discloses a drip type scent dispenser. Burgeson, U.S. Pat. No. 5,220,741 is also a drip-type device, but it also has a heating feature. Another dripping device is disclosed in Roberts, U.S. Pat. No. 5,299,376. Ward, U.S. Pat. No. Design 301,912 discloses a Deer Scent Holder.

The second type employs a heater to aid in diffusing the scent. U.S. Pat. No. 5,307,584, issued to Jarvis, is a screen walled canister which has an interior wick to absorb scent for diffusion. Easley, U.S. Pat. No. 4,771,563, is a canister type device that heats the scent. Daniels, U.S. Pat. No. 5,094,025, and Aurich, U.S. Pat. No. 5,161,646 are also scent heaters.

The final type of device employs a wick or other absorbent material. As indicated above, wicks are often employed in conjunction with scent heaters. Other devices only use a wick to draw the scent from a reservoir or hold it for diffusion. Fore, U.S. Pat. No. 5,327,667 discloses an adhesive strip mounting an absorbent pad. A brittle capsule of scent is captured between the strip and pad. The capsule is crushed to release the scent. Wilcox, U.S. Pat. No. 5,074,439 discloses a sealable pouch containing a pad impregnated with scent. The pouch is attached to a hunter by a lanyard. Kolf, U.S. Pat. No. Design 268,695 discloses a scent pad adapted to be tied to an object. Konietzki, U.S. Pat. No. 4,788,787 discloses a dispenser for fibrous line impregnated with a scent. Dehart, U.S. Pat. No. 4,302,899 discloses a sponge type scent pad and housing which can be mounted to a verity of locations. Speed, U.S. Pat. No. 5,263,274 discloses a pair of bottles linked by a length of wick. Scent is dispensed from one bottle to the other by hanging the bottle presently containing scent on a bracket. The scent is absorbed by the wick which diffuses a portion of it and conveys excess to the lower bottle. Stewart, U.S. Pat. No. 5,048,218 discloses a container and a rigid cylindrical core mounting a wick.

Each of the different types of prior art devices fail to address a problem. For example, drip type dispensers are wasteful of scent, which is often quite costly, as they drip the scent directly on the ground where it is absorbed and lost. Many of the prior art devices are bulky and/or cumbersome to use. In particular, the heater or canister type devices require setting up procedures which may not be practical when a hunter needs to avoid making noise. Additionally, transporting such devices may not be practical.

Hence, it is desirous to provide a game scent diffusion device which is convenient to use. In particular, the device needs to be easy to set up and transport. Preferably the device should be transported within the bottle of scent itself. The sealed bottle containing such a scent diffusion device could be carried in the hunter's pocket.

SUMMARY OF THE INVENTION

My Game Scent Diffusion Device is convenient to use. It can be stowed in the scent bottle when not in use, allowing the hunter to carry it in his pocket. It can also be easily deployed and hung from a nearby tree limb or the like.

The preferred embodiment of my game scent diffusion device comprises an inverted, generally "T" shaped member having a plurality of wick receptive orifices. A scent absorptive wick is woven through the orifices. The inverted "T" shaped member comprises an elongated body and a generally perpendicular crossbar. The crossbar can be springingly, temporarily bent to facilitate insertion of the device into the bottle. Once the device is inserted into the bottle the crossbar returns to its original shape. When the device is partially withdrawn from the bottle, the ends of the crossbar contact the neck of the bottle. Thusly, the bottle and diffusion device can be hung from a convenient location such as a tree limb. When so suspended, the bitter end of the saturated wick and a portion of the saturated wick woven through the orifices in the member are exposed to the ambient air. As a result, surrounding air currents can carry the scent in a natural manner, attracting game.

The preferred embodiment of my device employs an eyelet disposed within the bottle's cap to anchor the bitter end of the wick. With the wick so anchored, there is no need for the hunter to have any direct contact with the scent disposed on the wick. Once the cap is removed, the hunter can handle the cap, catching it in the fork of a tree or similarly suspending the bottle by wrapping the wick about a limb or other support.

An alternative embodiment of my invention comprises an elongated tab with a central orifice defined in it. This central orifice receives a length of wick, which can be anchored to the tab by either tying a knot in the bitter end or tying it around the tab itself. The tab is of sufficient length to engage the neck of a scent bottle to prevent removal of the wick and tab. The bitter end of the wick removed from the bottle provides a way to suspend the bottle and saturated wick from a tree limb or the like.

Therefore, a primary object of the present invention is to provide a game scent diffusion device.

Another object of the present invention is to provide a game scent diffusion device which is not bulky or cumbersome to carry.

Specifically, an object of the present invention is to provide a game scent diffusion device which can be carried in a pocket.

Another object of the present invention is to provide a game scent diffusion device which can be handled by a hunter without direct contact with the scent.

Another object of the present invention is to provide a device which can be used in conjunction with conventional scent bottles to diffuse scent.

An object of the present invention is to provide a game scent diffusion device which can be hung from a convenient tree limb or the like.

A related object of the present invention is to provide a game scent diffusion device which is lightweight.

Another object of the present invention is to provide a game scent diffusion device which takes advantage of ambient air currents to diffuse scent.

An object of the present invention is to provide a game scent diffusion device which does not waste scent.

A related object of the present invention is to provide a game scent diffusion device which allows excess scent to drain into the original bottle.

These and other objects and advantages of the present invention, along with features of novelty appurtenant thereto, will become apparent in the course of the following description.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views.

DETAILED DESCRIPTION

Figure 1:
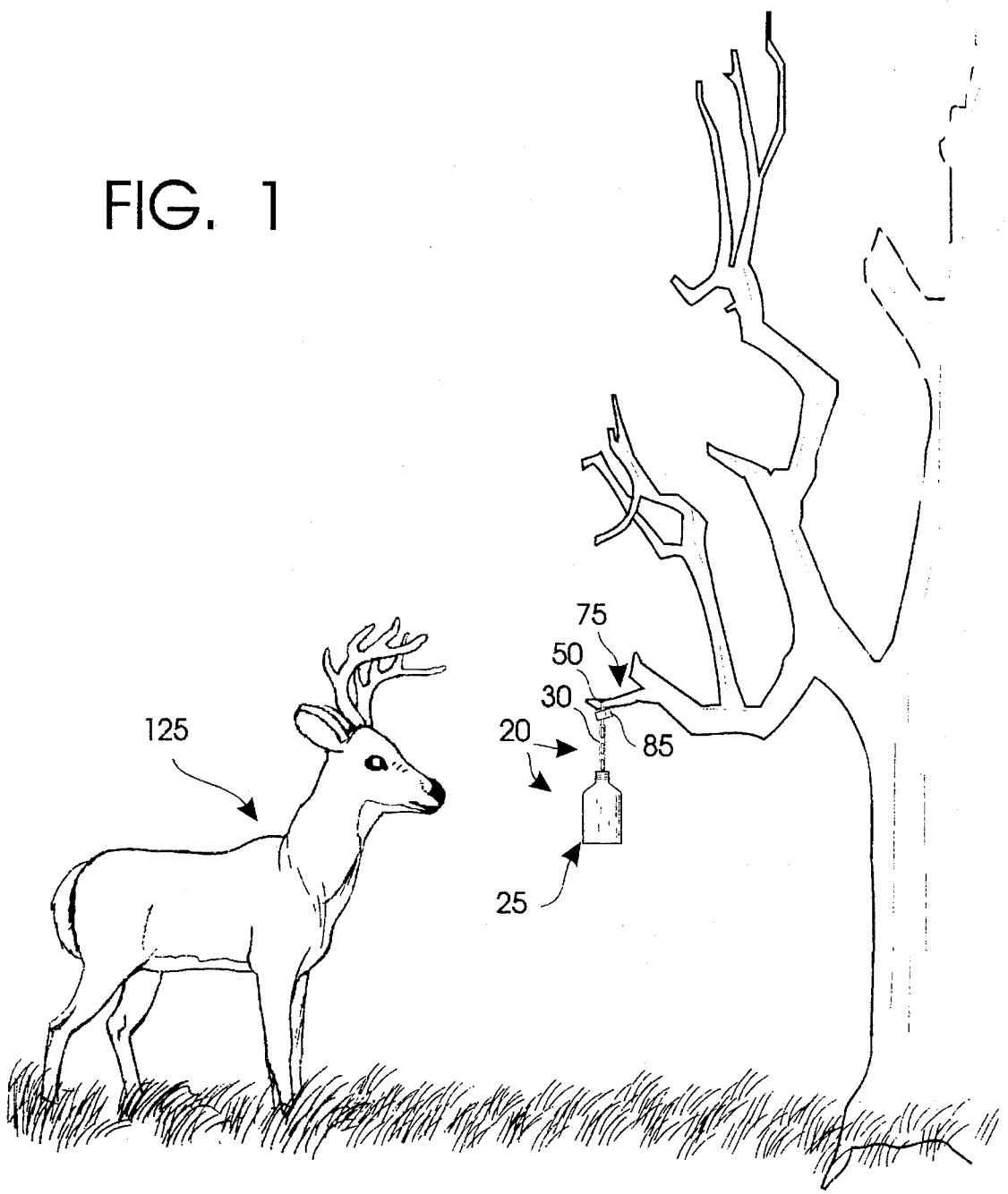
FIG. 1 is an environmental view of my Game Scent Diffusion Device in use.
Figure 3:
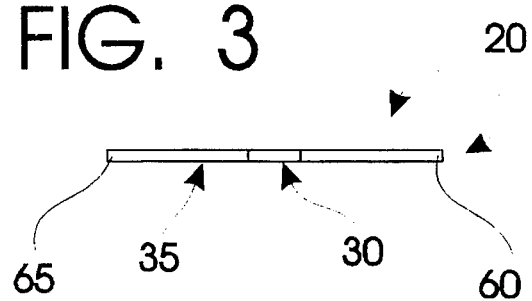
FIG. 3 is a top plan view of the preferred embodiment of my device.
Figure 2:
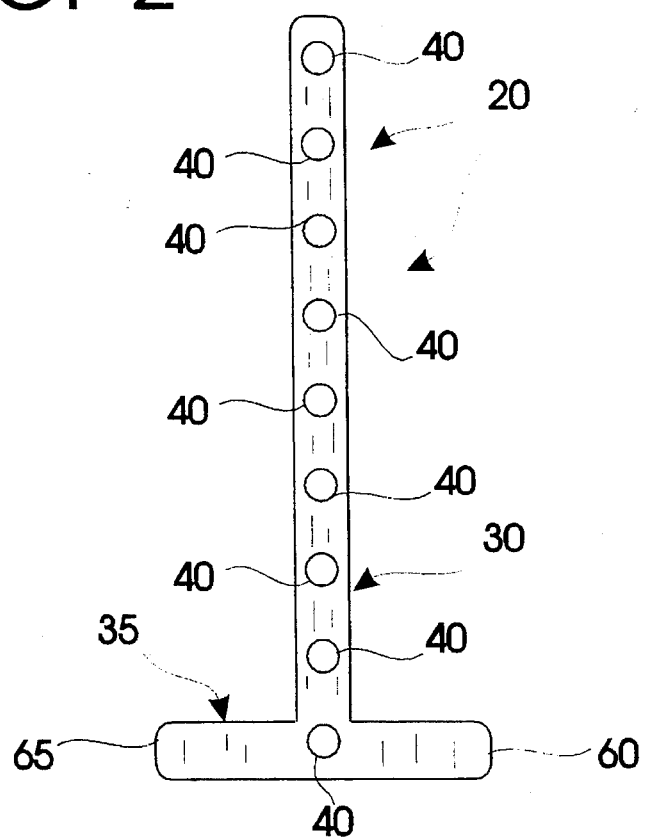
FIG. 2 is a front elevational view of the preferred embodiment of my device.
Figure 4:
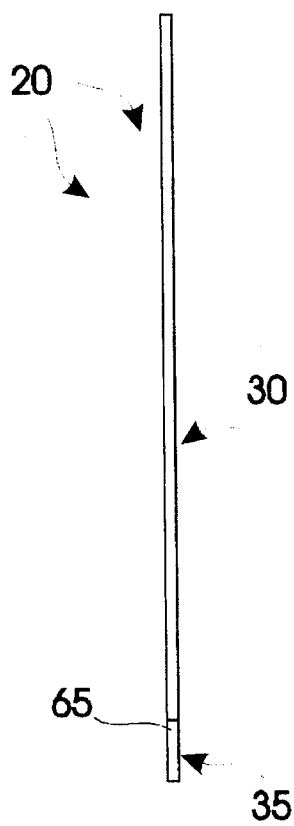
FIG. 4 is a side elevational view of the preferred embodiment of my device.
Figure 5:
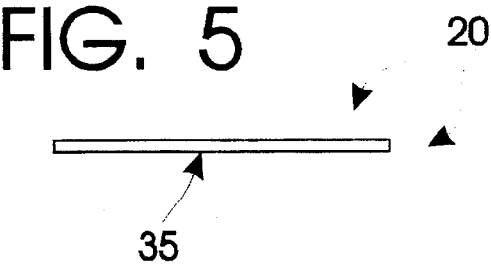
FIG. 5 is a bottom plan view of the preferred embodiment of my device.
Figure 6:
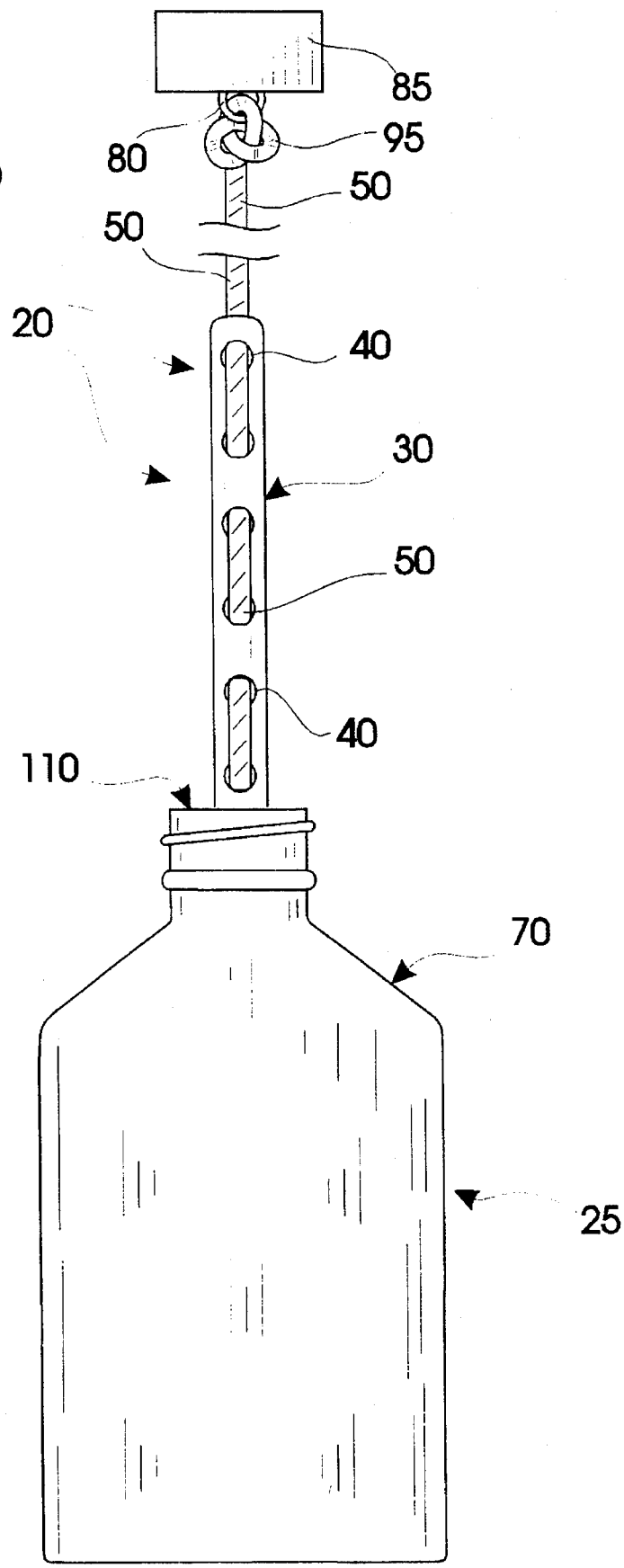
FIG. 6 is a partially fragmented, front elevational view illustrating the preferred embodiment of my device deployed in conjunction with a scent bottle.

With reference now to the accompanying drawings, the preferred embodiment of my Game Scent Diffusion Device is broadly designated by the reference numeral 20.

Figure 7:
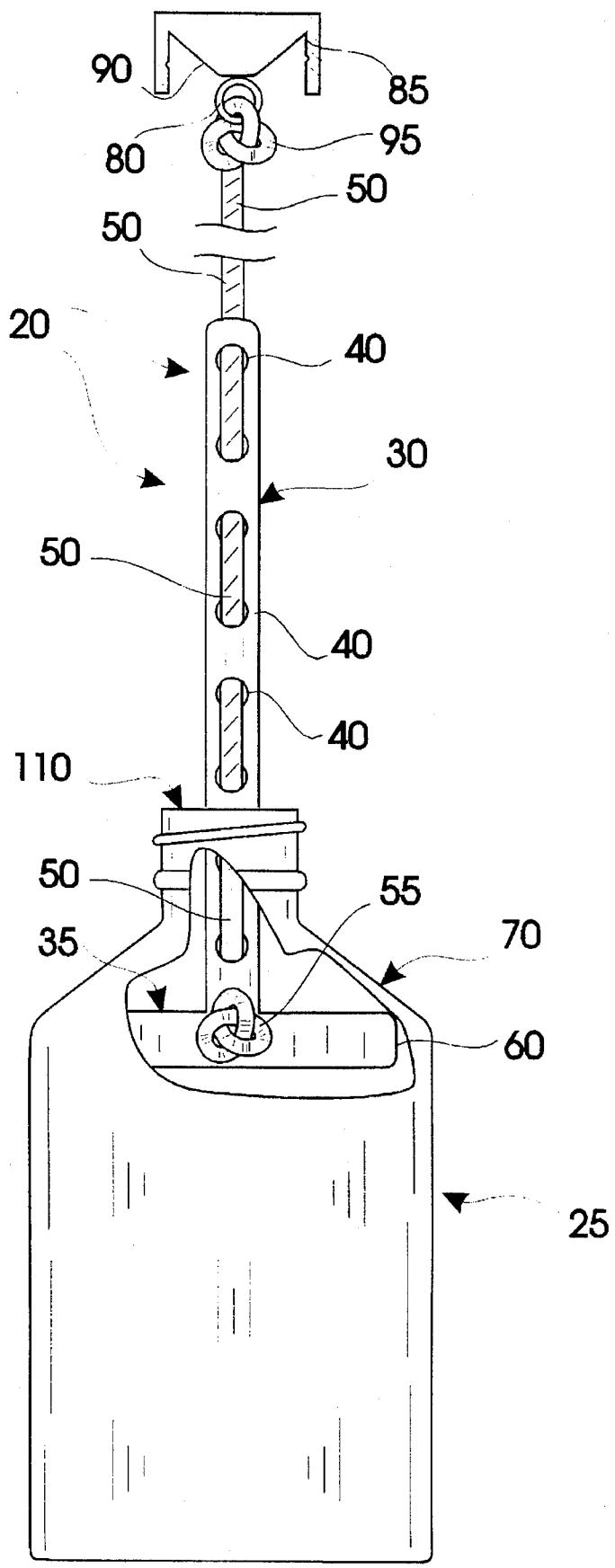
FIG. 7 is a further fragmented, front elevational view illustrating the preferred embodiment of my device deployed in conjunction with a scent bottle.

My game scent diffusion device 20 is intended to be disposed within a bottle 25 of game scent. It is partially withdrawn to diffuse scent. As best seen in FIGS. 2 through 5, the device 20 is an inverted "T" shaped member comprised of an elongated body portion 30 and a generally perpendicular crossbar portion 35. It is preferably constructed of a resilient material. The body portion 30 defines a plurality of orifices 40 along its length. The orifices 40 are intended to receive a fibrous wick 50 to absorb scent. A wick 50 can be woven through the orifices 40 and a knot 55 tied in the bitter end adjacent the crossbar portion 35. The ends 60, 65 of the crossbar portion 35 can be temporarily, springingly bent together to allow the device 20 with its attached wick 50 to be inserted into the bottle 25. Once the device 20 is inserted, the crossbar 35 springs back to its original shape, FIGS. 7 and 8. When the device 20 is partially withdrawn from the bottle 25, the ends 60, 65 of the crossbar portion 35 contact the neck 70 of the bottle 25 preventing complete removal of the device 20 and, allowing the bottle 25 to be suspended by the wick 50. The bitter end of the wick 50 outside the bottle 25 can be tied to a convenient location such as a tree limb 75, FIG. 1. When suspended, a section of wick 50 and a portion of the wick 50 woven through the orifices 40 in the body portion 30 of the device 20 is exposed to the ambient air.

In the preferred embodiment, an eyelet 80 is disposed within the bottle's cap 85. Preferably, the eyelet 80 can be screwed directly into the plastic insert 90 that can commonly be found within scent bottle caps 85. The bitter end 95 of the wick 50 outside the bottle 25 can be tied to the eyelet 80. Once removed, the cap 85 can be used by the hunter to handle the wick 50 extending from the scent diffusion device 20 and bottle 25. The cap 85 can be caught in the fork of a tree or the wick 50 can be wrapped around a tree limb 75 with the hunter only handling the cap 85.

Figure 9:
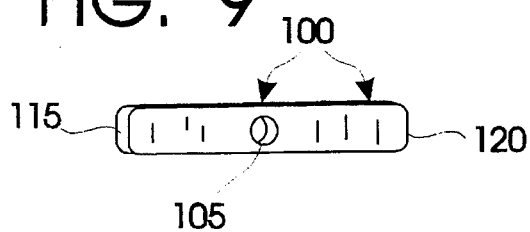
FIG. 9 is a front isometric view of an alternative embodiment of my device.
Figure 10:
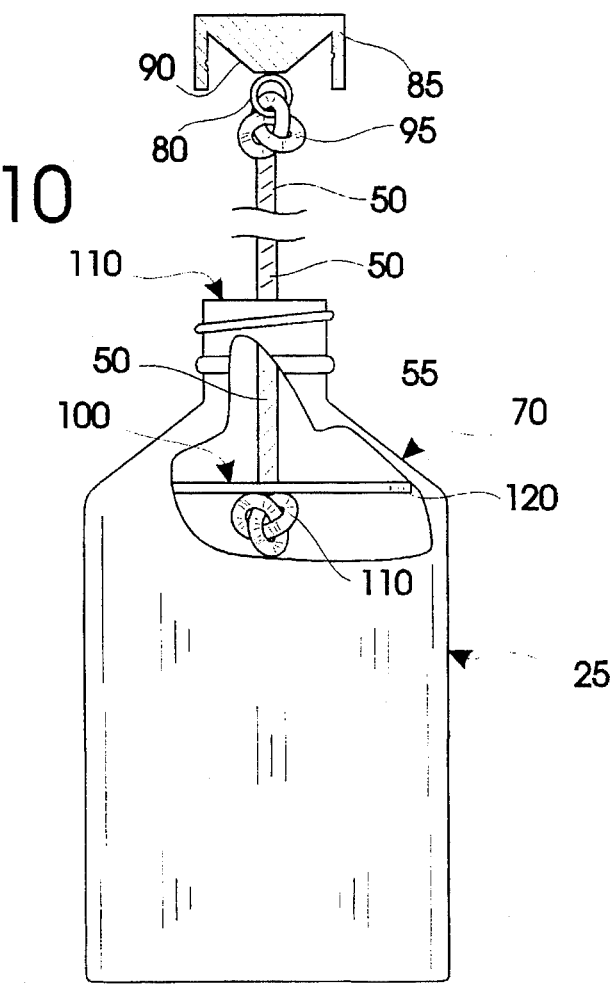
FIG. 10 is a partially fragmented, front elevational view illustrating the alternative embodiment of my device deployed in conjunction with a scent bottle.

The alternative embodiment illustrated in FIGS. 9 and 10 is comprised of an elongated tab 100 defining a cental orifice 105. The tab 100 is longer than the width of the mouth 110 of a conventional scent bottle 25. The wick 50 is passed through the central orifice 105 and preferably, a knot 110 is tied in the bitter end to suspend the scent bottle 25, as illustrated in FIG. 10. Alternatively, the wick 50 can be anchored to the tab 100 by tying it around the tab 100 itself, passing it through the orifice 105. Once the wick 50 is anchored to the tab 100, the tab 100 can be turned on end and inserted into the bottle 25. As the wick 50 is withdrawn the ends 115, 120 of the tab 100 engage the neck 70 of the scent bottle 25 to prevent removal of the wick 50 and tab 100. The bitter end of the wick 50 can be anchored to an eyelet 80 as with the preferred embodiment 20.

Figure 8:
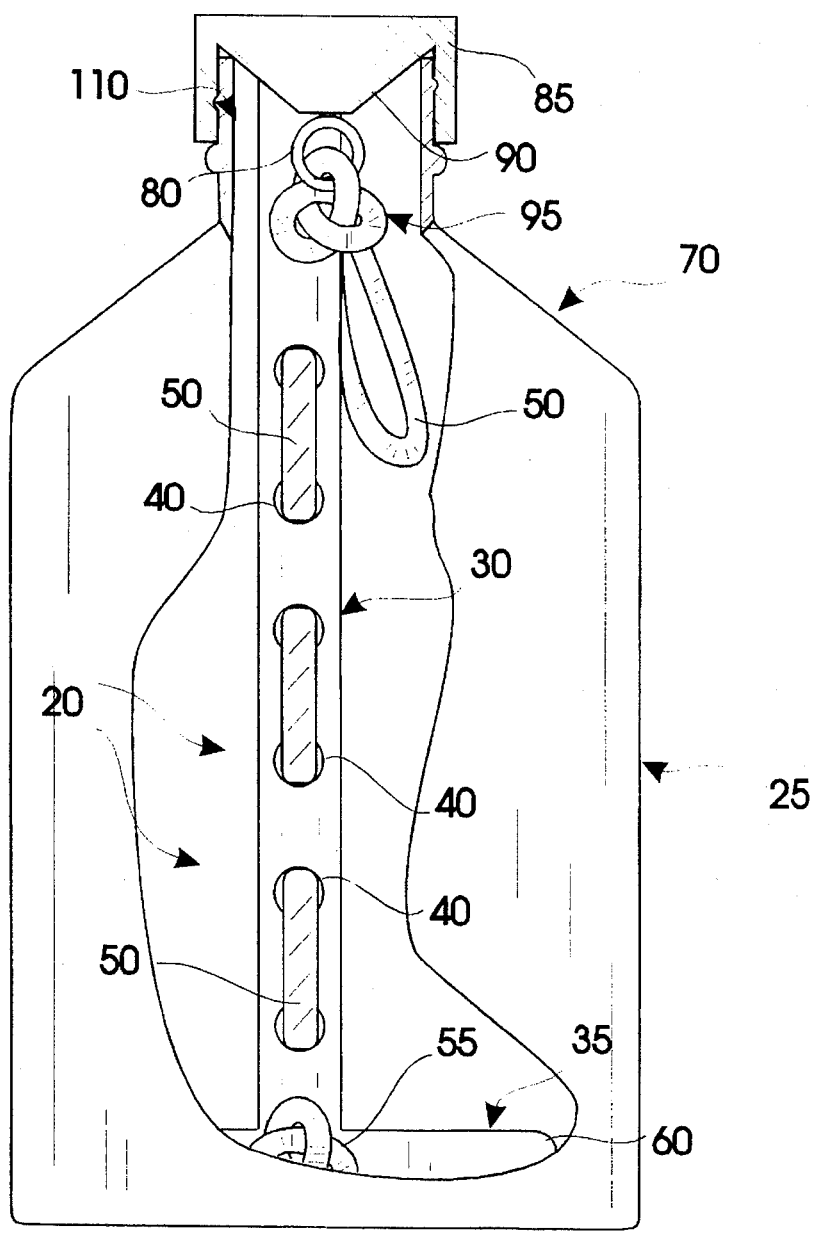
FIG. 8 is an enlarged, partially fragmented, front elevational view illustrating the preferred embodiment of my device stored in a scent bottle.

My game scent diffusion device is convenient to use. It can be carried in the scent bottle 25 when not in use, as illustrated in FIG. 8, allowing the hunter to carry it in his pocket. When deployed and hung from a nearby tree limb 75 or the like, ambient air currents diffuse the scent captured on the wick 50, attracting game 125. Excess liquid scent on the wick 50 drains into the bottle 25 thereby avoiding waste.

From the foregoing, it will be seen that this invention is one well adapted to obtain all the ends and objects set forth herein, together with other inherent advantages.

It will be understood that certain features and subcombinations are of utility and may be employed without reference to other features and subcombinations. This is contemplated by and is within the scope of the claims.

As many possible embodiments may be made of the invention without departing from the scope thereof. It is to be understood that all matter herein set forth or shown in the accompanying drawings is to be interpreted as illustrative and not in a limiting sense.

What is claimed is:

1. A game scent diffusion device comprising:
   a bottle for containing liquid scent, said bottle having a relatively narrow mouth and a cap adapted to be disposed over said mouth;
   an inverted generally "T" shaped wick receptive member adapted to be disposed within said bottle, said member comprising:
   an elongated flexible body portion comprising an upper end and a lower end;
   a flexible crossbar portion extending generally perpendicularly from the lower end of said body portion, said crossbar portion having opposite ends, said ends adapted to be springingly, temporarily bent toward one another to facilitate insertion of said member into said bottle, said ends, once said member is inserted, contacting a relatively narrow neck of said bottle when said member is partially withdrawn from said bottle; and, a plurality of wick receptive orifice defined along said body;

an absorptive wick woven through said orifices, said wick extending from said body to be externally secured to suspend said bottle with said member partially withdrawn from said bottle; and, an eyelet disposed within said cap to anchor a bitter end of said wick to facilitate suspension of said device.

2. The scent diffusion device as defined in claim 1 further comprising a conical shaped seal disposed within said cap to threadably receive said eyelet.

3. The scent diffusion device as defined in claim 2 wherein said bottle contains doe scent.

4. A game scent diffusion device comprising:

a bottle for containing liquid doe scent, said bottle having a relatively narrow mouth and a cap adapted to be disposed over said mouth;

an inverted generally "T" shaped wick receptive member adapted to be disposed within said bottle, said member comprising:

an elongated flexible body portion comprising an upper end and a lower end;

a flexible crossbar portion extending generally perpendicularly from the lower end of said body portion, said crossbar portion having opposite ends, said ends adapted to be springingly, temporarily bent toward one another to facilitate insertion of said member into said bottle, said ends, once said member is inserted, contacting a relatively narrow neck of said bottle when said member is partially withdrawn from said bottle; and, a plurality of wick receptive orifice defined along said body; and, an absorptive wick woven through said orifices, said wick extending from said body to be externally secured to suspend said bottle with said member partially withdrawn from said bottle.

5. The scent diffusion device as defined in claim 4 further comprising an eyelet disposed within said cap to anchor a bitter end of said wick to facilitate suspension of said device.

6. The scent diffusion device as defined in claim 5 further comprising a conical shaped seal disposed within said cap to threadably receive said eyelet.

7. The scent diffusion device as defined in claim 6 wherein said bottle contains doe scent.

8. A game scent diffusion device comprising:

a bottle for containing liquid scent, said bottle having a relatively narrow mouth and a cap adapted to be disposed over said mouth, a conical shaped seal disposed within said cap and an eyelet threaded into said seal within said cap;

an inverted generally "T" shaped wick receptive member adapted to be disposed within said bottle, said member comprising:

an elongated flexible body portion comprising an upper end and a lower end;

a flexible crossbar portion extending generally perpendicularly from the lower end of said body portion, said crossbar portion having opposite ends, said ends adapted to be springingly, temporarily bent toward one another to facilitate insertion of said member into said bottle, said ends, once said member is inserted, contacting a relatively narrow neck of said bottle when said member is partially withdrawn from said bottle; and, a plurality of wick receptive orifice defined along said body; and, an absorptive wick woven through said orifices, said wick extending from said body to be secured to said eylet in said cap to suspend said bottle with said member partially withdrawn from said bottle.

* * * * *